United States Patent
Sasaki et al.

[11] Patent Number: 6,050,948
[45] Date of Patent: Apr. 18, 2000

[54] ULTRASOUND DOPPLER DIAGNOSTIC APPARATUS

[75] Inventors: Takuya Sasaki; Ryoichi Kanda, both of Otawara, Japan

[73] Assignee: Kabushiki Kaisha Toshiba, Kawasaki, Japan

[21] Appl. No.: 09/116,963

[22] Filed: Jul. 17, 1998

[30] Foreign Application Priority Data

Jul. 18, 1997 [JP] Japan .................................. 9-194041

[51] Int. Cl.<sup>7</sup> ........................................................ A61B 8/00
[52] U.S. Cl. ............................................ 600/453; 600/454
[58] Field of Search .................................. 600/440, 441, 600/443, 447, 453, 454–457; 364/510; 128/916

[56] References Cited

U.S. PATENT DOCUMENTS

| | | | |
|---|---|---|---|
| 4,373,532 | 2/1983 | Hill et al. | 600/437 |
| 5,146,414 | 9/1992 | McKown et al. | 364/510 |
| 5,287,753 | 2/1994 | Routh et al. . | |
| 5,634,465 | 6/1997 | Schmiesing et al. . | |
| 5,647,366 | 7/1997 | Weng | 600/455 |
| 5,935,074 | 8/1999 | Mo et al. | 600/454 |

FOREIGN PATENT DOCUMENTS

| | | |
|---|---|---|
| 6-327672 | 11/1994 | Japan . |
| 7-241291 | 9/1995 | Japan . |
| 9-521 | 1/1997 | Japan . |

*Primary Examiner*—William E. Kamm
*Assistant Examiner*—Ali M. Imam
*Attorney, Agent, or Firm*—Oblon, Spivak, McClelland, Maier & Neustadt, P.C.

[57] ABSTRACT

A technique is disclosed for accurately tracing a maximum or minimum frequency in each of Doppler-shifted frequency spectra arranged in a sequential order of time on the time axis as an M-mode Doppler image. The maximum or minimum frequency is picked up by thresholding and hence the trace accuracy depends on a threshold. The threshold is determined based on the average brightness of a sample region in which noise is dominant. Therefore, the capability of discriminating between signal and noise components improves, allowing the trace accuracy to be improved.

20 Claims, 8 Drawing Sheets

ULTRASOUND DOPPLER DIAGNOSTIC APPARATUS

BACKGROUND OF THE INVENTION

The present invention relates to an ultrasound Doppler diagnostic apparatus which has a function of displaying Doppler-shifted frequency spectrum variations with time which is known as the so-called M mode.

The principal medical application of ultrasound is the ultrasound pulse reflection method. This method has a distance resolution and allows soft tissues in a living body to be visualized. In comparison with X-ray diagnostic apparatus, X-ray computerized tomography apparatus, magnetic resonance imaging apparatus, and scintillation camera apparatus, the method has features of allowing real-time display, being small and inexpensive, and being safe from exposure to X-rays or the like.

These features exhibit a remarkable effect in obstetrics and gynecology. An ultrasound apparatus is carried to bedside. The ultrasonic transducer is put to the abdomen of a pregnant woman and then the fetus is imaged.

The pulse reflection method may be used together with the Doppler method, which analyzes the Doppler shift of an echo signal utilizing the so-called Doppler effect that the frequency of ultrasound waves shifts when reflected from blood corpuscles and the like. The Doppler-shifted frequency fd is given by $$fd = \{(2 \cdot v \cdot \cos \theta \cdot fc)/c\} \cdot fc$$

where fc is the center frequency of an ultrasound beam, f is the receiving frequency, v is the bloodstream velocity, $\theta$ is the angle between the ultrasound wave and the bloodstream, and c is the velocity of sound within living body.

The pulsed Doppler method is divided into the color flow mapping (CFM) method and the M-mode method. The CFM permits the bloodstream in a sectional plane to be represented with the average velocity, variance, and power. In the M-mode method, Doppler-shifted frequency spectra relating to Doppler-shifted frequencies contained in echo signals from a desired position are generated in sequence at regular intervals. The Doppler-shifted frequency spectrum provides a relationship between power and frequency. In the M mode, multiple Doppler spectra are arranged on the time axis. The display brightness is modulated with power. In FIG. 1 there is illustrated a Doppler image in the M mode, which is composed of Doppler-shifted frequency spectra arranged in time sequence.

In the M mode, tracing the maximum frequencies or the centroid frequencies in the Doppler-shifted frequency spectra in time sequence frequently furnishes doctors with effective information for diagnosis (refer to FIGS. 2 and 3).

The tracing accuracy depends on the capability of discriminating between signal and noise components. The discrimination is performed based on a threshold. The method of determining the threshold is roughly divided into a method that is dependent on the brightness of bloodstream signals and a method that is dependent on noise levels.

With a typical example (A) of the former method, a value that is a predetermined level (dB) below the maximum brightness of bloodstream is set as a threshold (Japanese Unexamined Patent Publication No. 7-30361). With a typical example (B) of the latter method, a histogram is first obtained which represents a brightness distribution within a region in the vicinity of the baseline which is considered to have few bloodstream signals and then the brightness which corresponds to the frequency half the maximum frequency in the histogram is set as a threshold (Japanese Unexamined Patent Publication No. 7-241291).

Also, there is an example (C) in which a threshold is determined according to signal gain or bandwidth characteristics (U.S. Pat. No. 5, 634, 465, Japanese Unexamined Patent Publication No. 9-521).

With the method (A), the threshold depends strongly on the signal-to-noise (S/N) ratio of a Doppler signal. If, therefore, the S/N ratio is low, the maximum-frequency curve will contain spikes as shown in FIG. 4. With the method (B), when bloodstream signals are mixed in that region, the threshold cannot be set properly. The probability of bloodstream signals mixing in that region becomes high, particularly in strong pulsation situations. With the method (C), since the correlation of random noise to the characteristics is unstable, the reliability of the threshold set cannot not be said to be very high.

The centroid frequency tracing has similar problems. In low S/N situations, a wrong line will be traced under the influence of noise as shown in FIG. 5.

Various feature quantities may be calculated out from these trace lines. With a trace line of low accuracy, the feature quantities may result in errors because it is impossible to accurately determine the contraction phase and the end of the dilation phase of the heart cycle required to calculate the feature quantities.

BRIEF SUMMARY OF THE INVENTION

It is an object of the present invention to provide an ultrasound Doppler diagnostic apparatus which permits noise-based errors associated with tracing maximum velocities of bloodstream to be reduced.

In the present invention, a threshold used to search for maximum or minimum frequencies is determined on the basis of the average brightness of a sample region in which noise is dominant. Thus, the capability of discriminating between noise and signal components is improved, resulting in increased accuracy of tracing the maximum or minimum frequencies.

In addition, the results of this accurate tracing are used to define the bloodstream range, so that the centroid frequencies are traced accurately within this range.

Moreover, specific events in the cardiac cycle can be identified on the basis of the resulting trace line with high accuracy.

Furthermore, markers indicating the accurately identified cardiac events can be displayed in conjunction with the trace line, providing effective diagnostic information.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

DETAILED DESCRIPTION OF THE INVENTION

Figure 1:
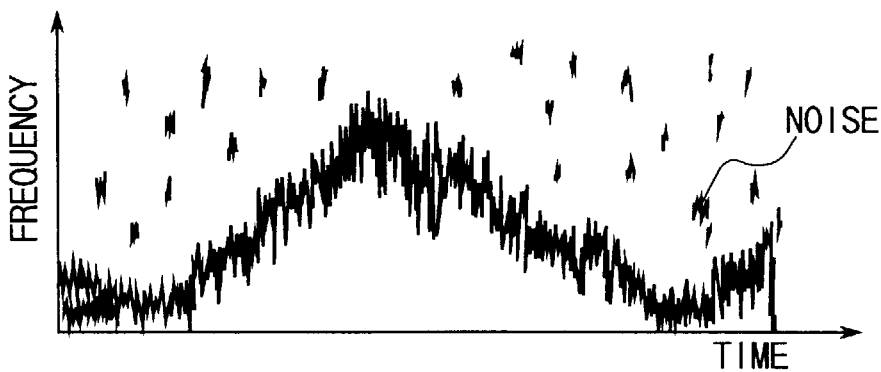
FIG. 1 shows a Doppler image which represents changes in Doppler-shifted frequency spectrum with respect to time in the prior art apparatus.
Figure 2:
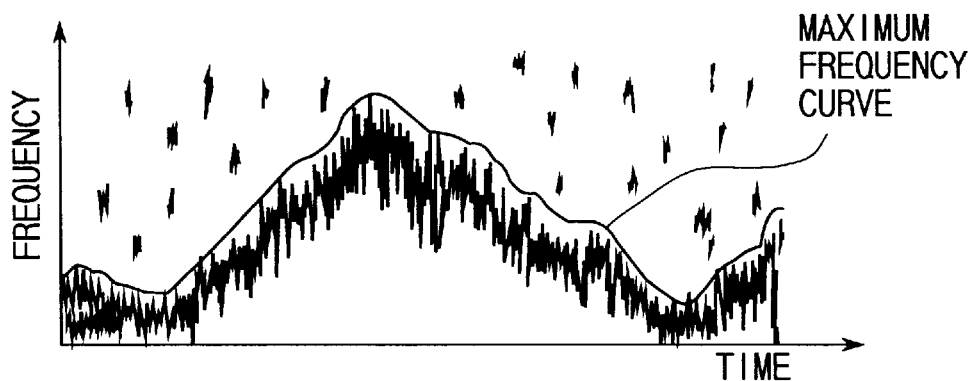
FIG. 2 shows a line that traces the maximum frequency in each Doppler-shifted frequency spectrum in the prior art apparatus.
Figure 3:
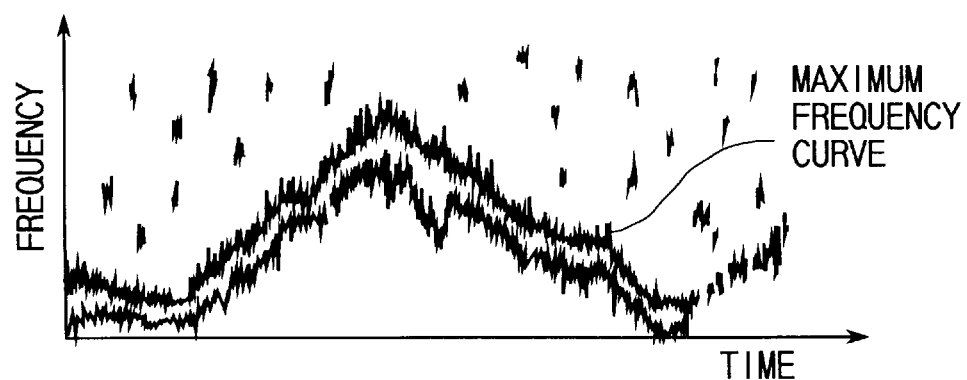
FIG. 3 shows a line that traces the centroid frequency in each Doppler-shifted frequency spectrum in the prior art apparatus.
Figure 4:
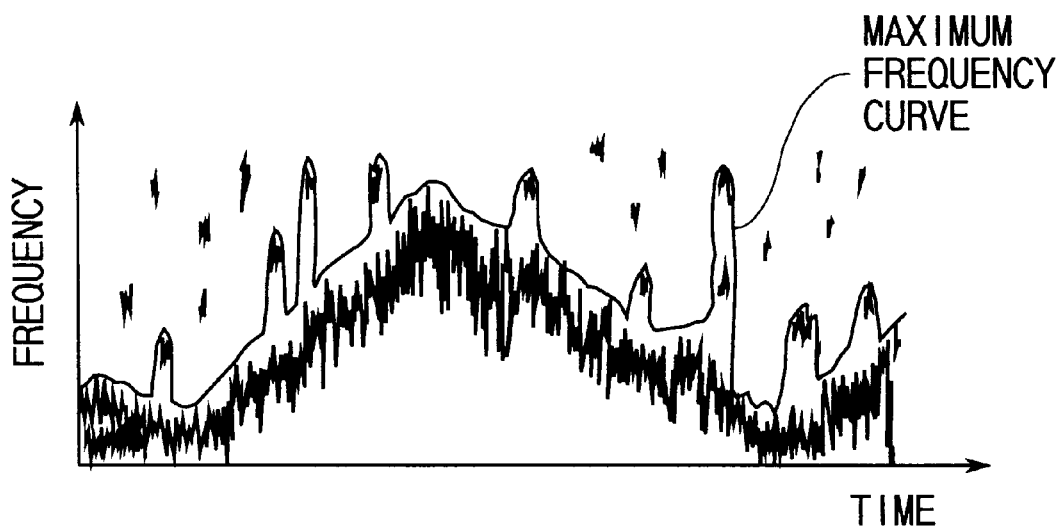
FIG. 4 shows maximum-frequency tracing errors in the prior art apparatus.
Figure 5:
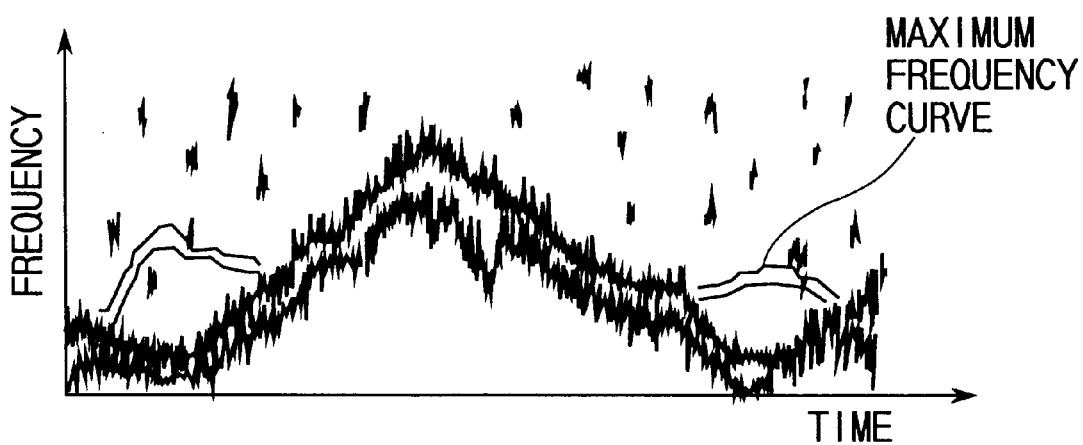
FIG. 5 shows centroid-frequency tracing errors in the prior art apparatus.
Figure 6:
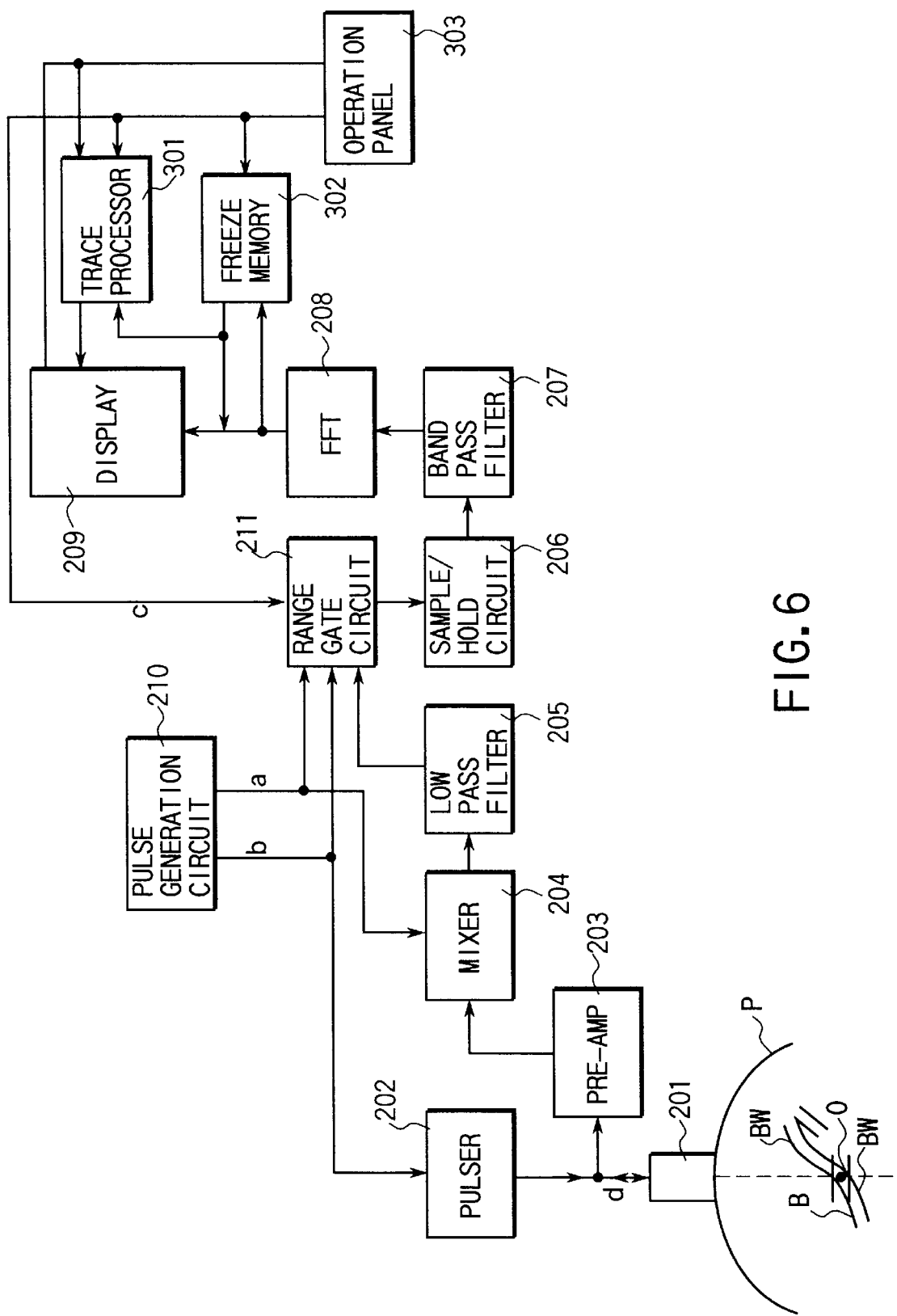
FIG. 6 is a block diagram of an ultrasound diagnostic apparatus embodying the present invention.
Figure 7:
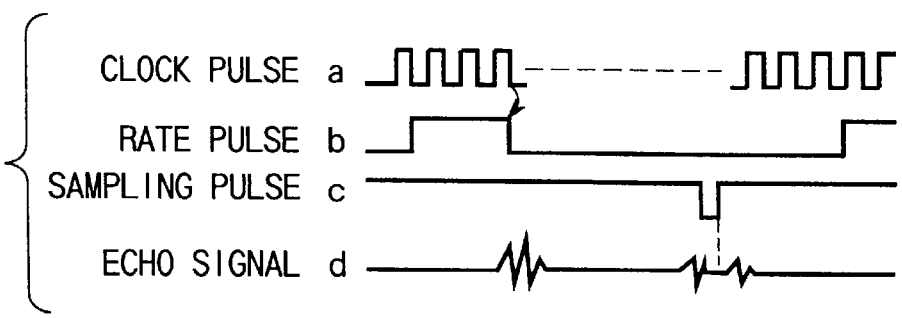
FIG. 7 is a timing diagram for use in explanation of the operation of the sample and hold circuit of FIG. 6.

Referring now to FIG. 6, there is illustrated an arrangement of an ultrasound diagnostic apparatus embodying the present invention. An ultrasonic transducer array or probe 201 has a number of transducer elements arranged at its tip. The transducer array may be of any type of sector, linear and convex scanning.

A pulse generator 210 outputs clock pulses (a) and rate pulses (b) produced by dividing the frequency of the clock pulses. The rate pulses triggers a pulser 202, which, when triggered, provides high-voltage, high-frequency drive pulses to the transducer elements of the ultrasonic probe 201. The probe, when driven, forms a pulsed beam of ultrasound, which travels in a human body under examination and is reflected from acoustic-impedance interfaces within the human body back to the probe 201. This echo mechanically vibrates the transducer elements of the probe 201. Thereby, electric echo signals (d) are produced.

The echo signals have Doppler-shifted frequency components. That is, when a pulse of ultrasound hits bloodstream (corpuscles), it is scattered by moving corpuscles and its frequencies are shifted. Thus, the center frequency fc of the ultrasonic beam is shifted by the Doppler frequency fd. Thus, the receiving frequency f reaches fc+fd. The Doppler frequency fd is represented by $$fd = (2 \cdot v \cdot \cos \theta \cdot fc)/c$$

where v is the velocity of bloodstream, θ is an angle between the ultrasonic beam and the blood vessel, and c is the velocity of sound.

Therefore, the detection of the Doppler frequency fd allows the component in the beam direction of the bloodstream velocity, i.e., v·cos θ, to be known.

A preamplifier 203 amplifies echo signals. A mixer 204 and a lowpass filter 205 quadrature-phase detect the amplified echo signals to form Doppler signals in which the Doppler frequency component fd predominates.

A range gate circuit 203 performs range gate processing on the Doppler signals so as to cut out Doppler signals corresponding to a desired depth. The rate gate timing is delayed by a time from the rate pulse (b). The delay time is obtained by dividing twice the depth of a sample volume set by an operator through an operating panel 303 by the velocity of sound.

The Doppler signals cut out by the range gate circuit 211 are applied via a sample and hold circuit 206 to a bandpass filter 207, which is adapted to remove from the Doppler signals clutter components as well as high-frequency components produced by the sample and hold circuit 206. Thereby, the Doppler frequency components resulting from bloodstream become predominant in the Doppler signals.

A frequency analyzer 208 makes a frequency analysis, such as fast Fourier transform (FFT), of the Doppler signals from the bandpass filter 207. Thereby, a Doppler-shifted frequency spectrum is calculated which reflects the bloodstream velocity distribution and represents a relationship between each frequency and power. Such Doppler-shifted frequency spectra are obtained in sequence at regular intervals and then arranged on the time axis. The power is brightness-modulated. Thereby, a Doppler image representing changes in Doppler-shifted frequency spectrum with respect to time is displayed on a display unit 209.

A freeze memory 302 is provided which, upon receipt of a freeze command from the operating panel 303, temporarily stores a specific Doppler image in order to freeze the display at that Doppler image.

A trace processor 301 has a function of tracing the maximum frequencies, the minimum frequencies, and the centroid frequencies, a function of identifying characteristic events (heart beat phases) in the cardiac cycle, such as a point of the maximum bloodstream velocity in the contraction phase of the heart cycle (the systole maximum velocity), a point of the end-of-diastole bloodstream velocity, a point of the minimum bloodstream velocity, and so on, and a function of displaying the trace line and cardiac event markers on the display unit 209 superimposed on the Doppler image.

The operating panel 303 is equipped with various function keys required as well as an image freeze switch and a pointing device, such as a truck ball or mouse, for setting a sample volume.

Figure 8:
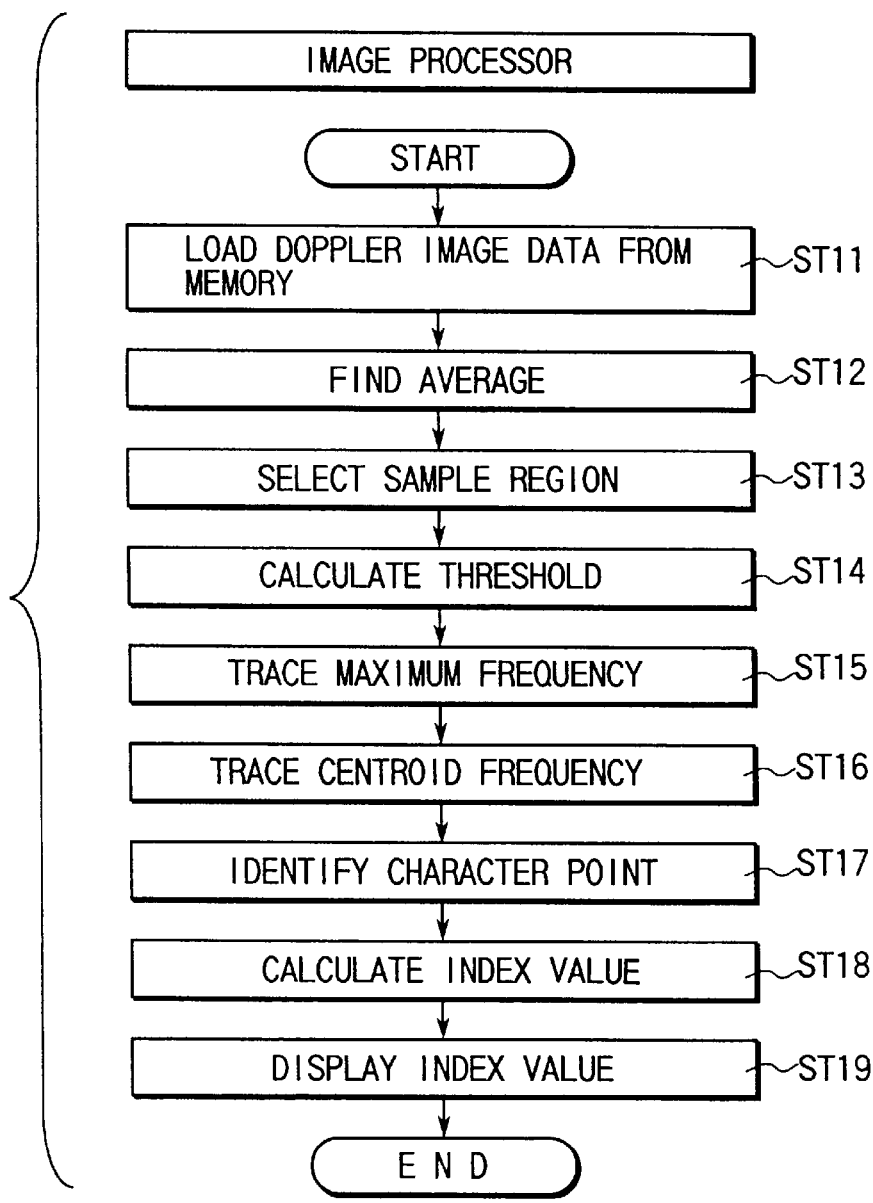
FIG. 8 is a flowchart illustrating the operation of the image processor of FIG. 6.

FIG. 8 shows the process flow of the trace processor 301.

Step S11: The Doppler image data is read from the freeze memory 302 into the trace processor 301.

Figure 9:
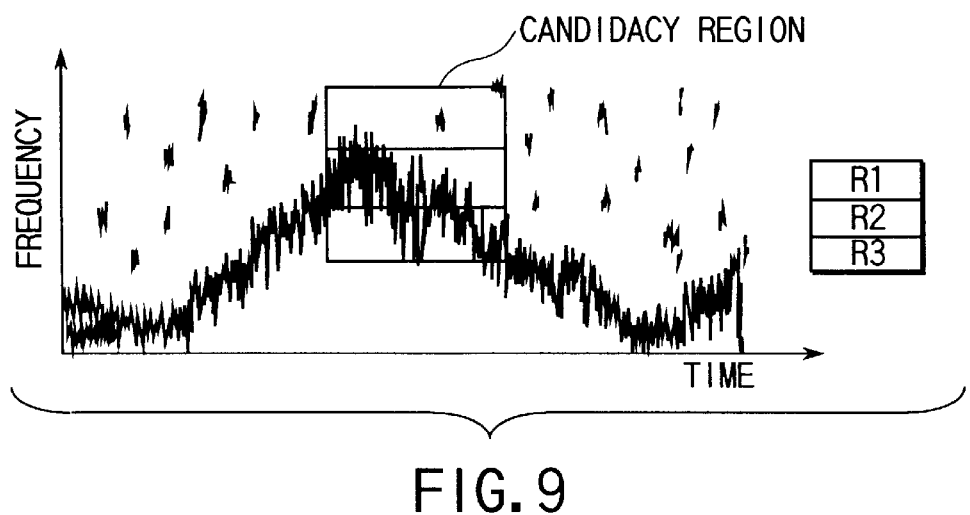
FIG. 9 shows an example of a sample region in step S13 of the flowchart of FIG. 8.
Figure 10:
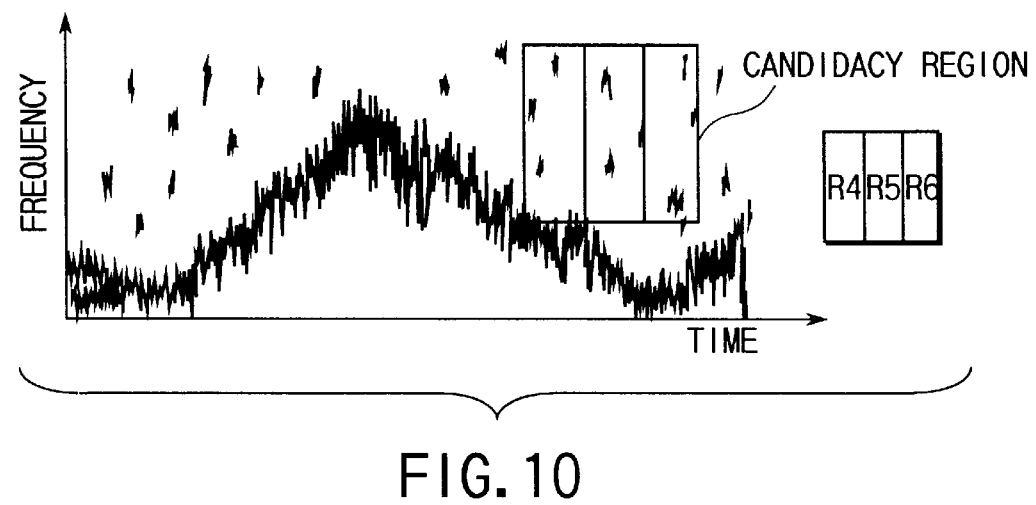
FIG. 10 shows another example of a sample region.
Figure 11:
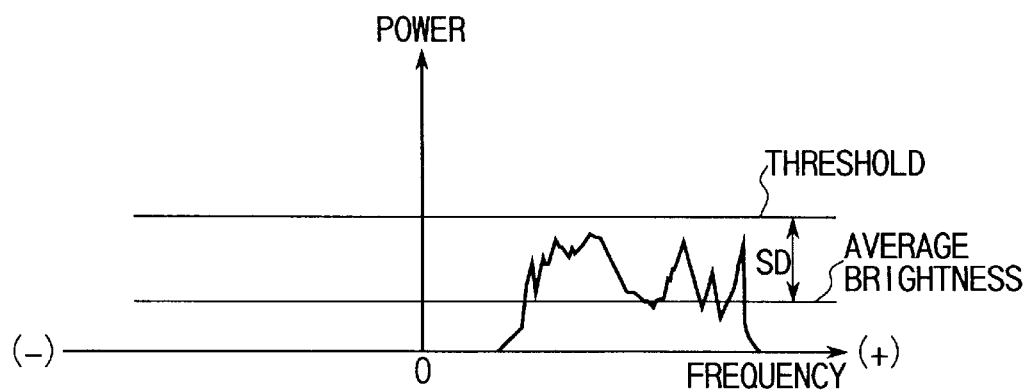
FIG. 11 is a diagram for use in explanation of the method of calculating the threshold in step S14 of FIG. 8.

Step S12: The average brightness is calculated for each of a plurality of candidate regions (six in this example) in the Doppler image. The average brightness is obtained by an arithmetic operation of dividing the sum of brightness levels of a plurality of pixels in each region by the pixel count. Candidate regions R1 to R6 are shown in FIGS. 9 and 10. The sizes of the candidate regions have been set in advance so that each region contains an equal number of pixels. Also, the shape and position of each candidate region have been set in advance. The three candidate regions R1, R2 and R3 are each designed in the form of a rectangle whose long side is parallel to the time (horizontal) axis and arranged in the direction of the frequency (vertical) axis. On the other hand, the three candidate regions R4, R5 and R6 are each designed in the form of a rectangle whose long side is parallel to the frequency axis and arranged in the direction of the time axis.

The regions R1 to R3 are shifted in position from the regions R4 to R6 so that they will not overlap.

Step S13: A candidate region which has the minimum average brightness is selected as a sample region. In the selected candidate region, noise components are present in much larger quantities and bloodstream signal components are present in smaller quantities than in any other candidate region. The reason is that the noise components are unstable in magnitude and vary at random, whereas bloodstream signal components are stable. Instead of automatically selecting a sample region from among candidate regions, the operator may specify through the operating panel 303 a region that is considered to contain noise components in large quantities and bloodstream signal components in small quantities in any position, in any size, and in any shape.

Step S14: By adding the standard deviation SD of brightness values in the selected sample region to its average brightness AB, the threshold TH is calculated to be $$TH=AB+SD\times\alpha$$

where $\alpha$ is a coefficient.

It is preferable to allow the operator to change the coefficient a to an arbitrary value, depending on the tracing accuracy.

Figure 12:
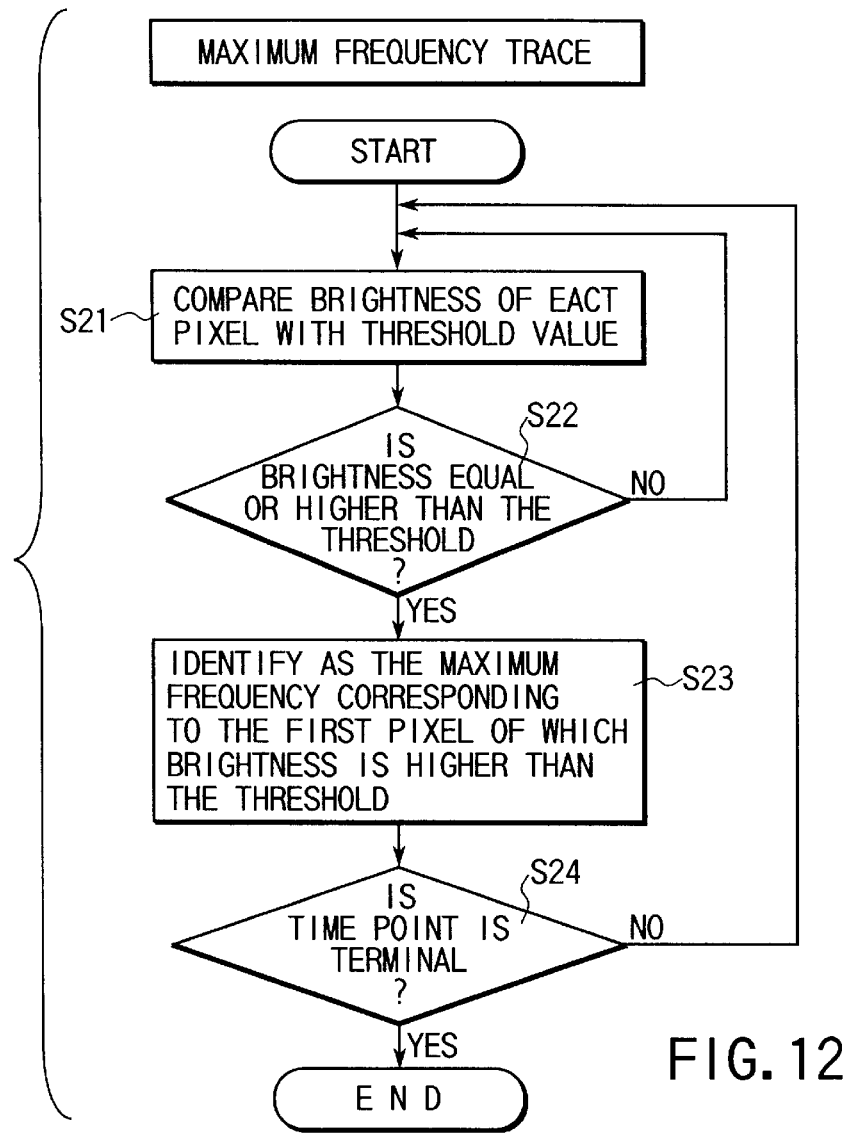
FIG. 12 is a detailed flowchart for step S15 of FIG. 8.
Figure 13:
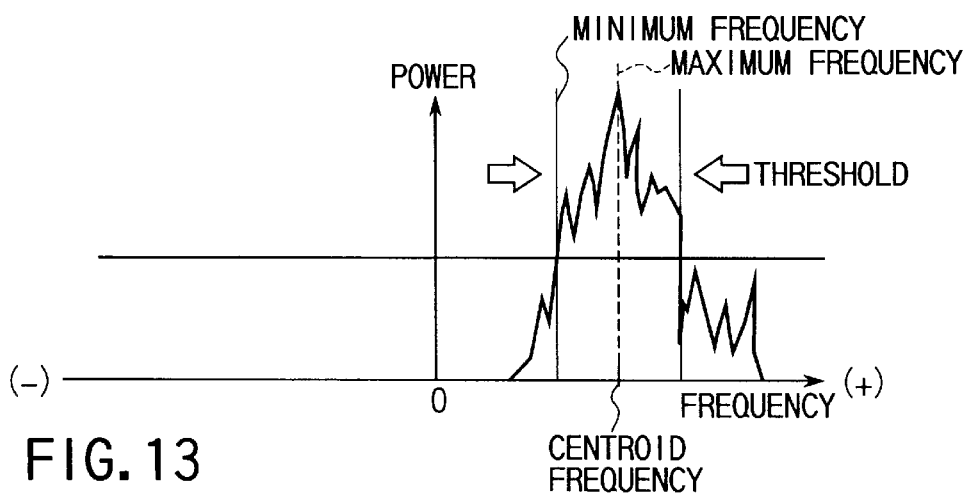
FIG. 13 is a diagram for use in explanation of step S21 of FIG. 12.

Step S15: The maximum and minimum frequencies at each point of time in the Doppler image (i.e., in each Doppler-shifted frequency spectrum) are each traced along the time axis on the basis of the threshold determined in step S14. FIG. 12 shows a maximum-frequency tracing technique, and FIG. 13 shows a Doppler-shifted frequency spectrum at a certain point of time as a supplemental drawing. In step S21, the brightness of each pixel is compared with the threshold in sequence from the high-frequency side.

In steps S22 and S23, the frequency for the first pixel whose brightness exceeds the threshold is picked up as the maximum frequency. In the case of tracing the minimum frequencies, the brightness of each pixel is compared with the threshold in sequence from the low-frequency side and the frequency for the first pixel whose brightness exceeds the threshold is picked up as the minimum frequency.

By repeating such processes in steps S21, S22 and S23 for each point of time (i.e., for each Doppler-shifted frequency spectrum) (step S24), the maximum-frequency trace line and the minimum-frequency trace line are obtained.

Figure 14:
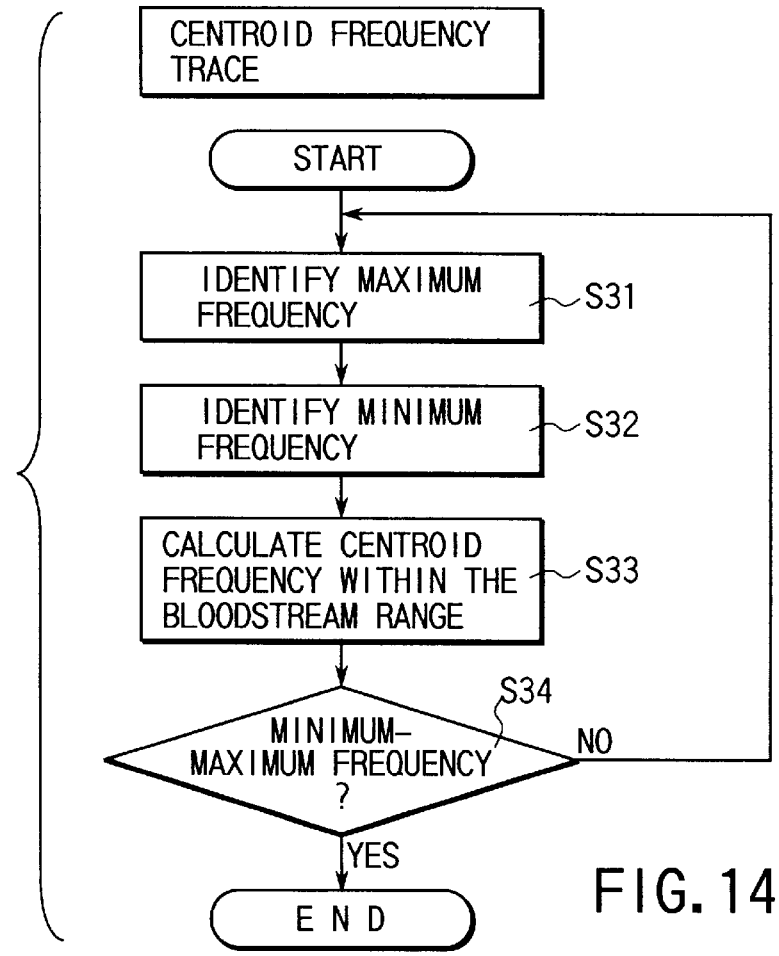
FIG. 14 is a detailed flowchart for step S16 of FIG. 8.
Figure 15:
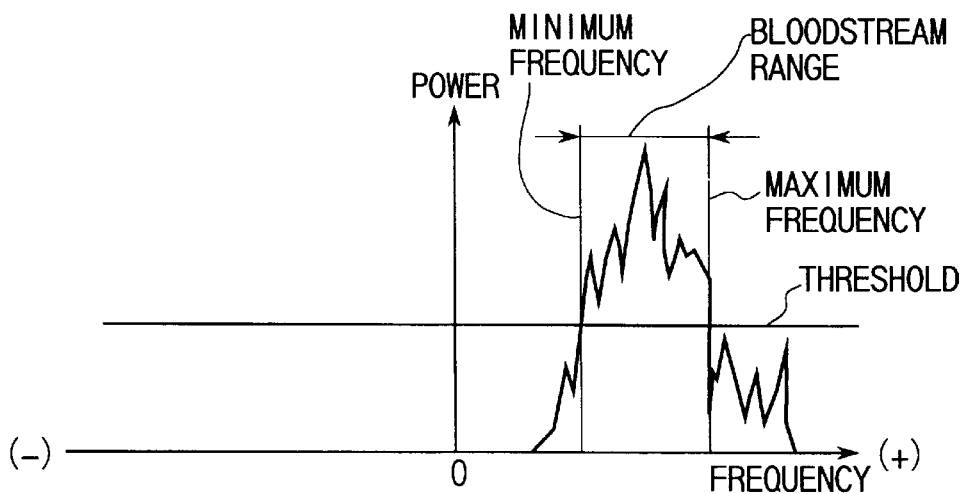
FIG. 15 is a diagram for use in explanation of step S16 of FIG. 8.

Step S16: the centroid frequencies are traced on the basis of the maximum-frequency trace line and the minimum-frequency trace line. FIG. 14 shows a centroid-frequency tracing technique, and FIG. 15 shows a Doppler-shifted frequency spectrum at a certain point of time as a supplemental drawing. The region between the maximum-frequency trace line and the minimum-frequency trace line is the frequency range over which bloodstream components are distributed. In steps S31 and S32, the bloodstream distribution range is defined. Then, in step S33, the centroid frequencies are calculated on the defined bloodstream range. Such processes in steps S31, S32 and S33 are carried out for each point of time, i.e., for each Doppler-shifted frequency spectrum. In this manner, the centroid-frequency trace line is obtained.

Although the bloodstream range is defined between the maximum and minimum frequencies to calculate the centroid frequency, the centroid frequency may be obtained by first extracting a group of pixels having brightness levels above the threshold determined in step S13 of FIG. 8 and then calculating the centroid frequency on the extracted group of pixels. Alternatively, the centroid frequency may be obtained by weighting in the direction of the frequency axis.

Figure 16:
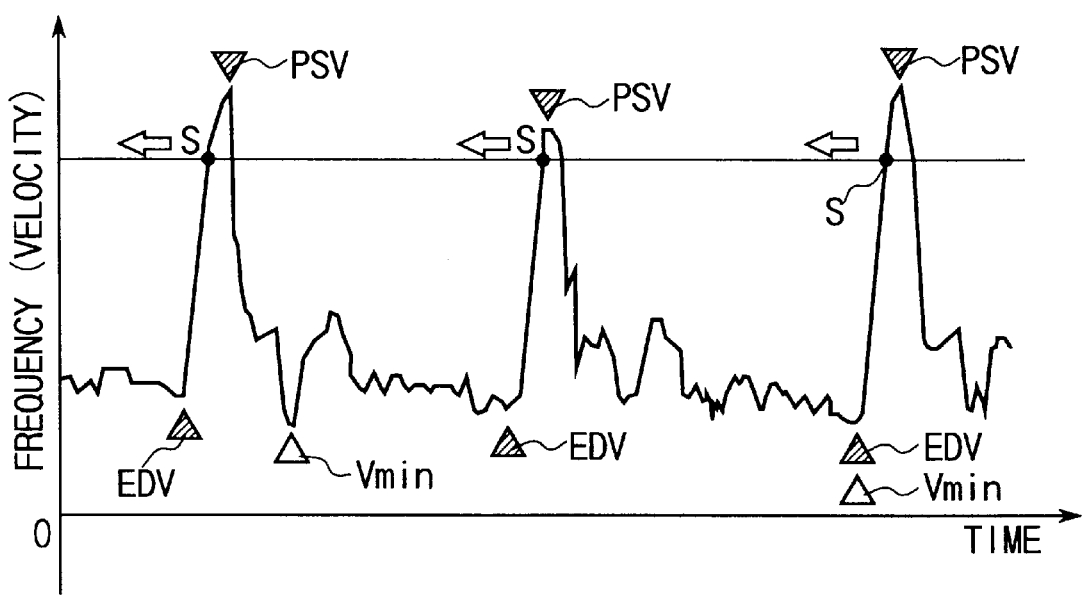
FIG. 16 shows a display example in step S19 of FIG. 8.

Step S17: As shown in FIG. 16, the systole maximum velocity point (PSV), the end-of-diastole velocity point (EDV), and the minimum velocity point (Vmin) in one cardiac cycle are identified on the basis of the maximum-frequency, the minimum-frequency or the centroid-frequency trace line.

First, the maximum value (the maximum frequency) in the maximum-frequency trace line is multiplied by a predetermined coefficient of, for example, 0.8, thereby obtaining a threshold for determining the contraction phase in the cardiac cycle. A period of time that the maximum-frequency trace line exceeds the calculated threshold is determined as the contraction phase. The systole maximum velocity (PSV) and the end-of-diastole velocity (EDV) are identified on the basis of the contraction phase thus determined.

First, the PSV is identified as the maximum point of the trace line in the contraction phase of the heart. The EDV is identified as a minimum point that first appears when the trace line is followed backward from the starting point S of the contraction phase. The following of the trace line may start from the PSV point in place of the starting point S of the contraction phase. In searching the trace line for the minimum point with the PSV point as the starting point, the trace line may fluctuate greatly in the neighborhood of the PVS point. In such a case, EDV misrecognition might occur. However, if the search is started at the starting point S of the contraction phase of the heart, such misrecognition will not occur. The minimum velocity point (Vmin) is identified as a point at which the trace line is at the lowest level between adjacent EDV points.

Step S18: Bloodstream indexes, compression rate etc., are calculated from the PSV, EDV, and Vmin identified in step S17.

Step S19: The trace line that follows the maximum frequency, the minimum frequency or the centroid frequency of each Doppler-shifted frequency spectrum is displayed on the display unit 209 together with PSV, EDV and Vmin markers. These markers are placed in their respective positions associated with the trace line.

The trace processor may be implemented in software or hardware.

Although the preferred embodiment of the present invention has been disclosed and described, it is apparent that other embodiments and modifications are possible.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. An ultrasound Doppler diagnostic apparatus comprising:

means for transmitting pulsed beams of ultrasound to a subject under examination and receiving echo signals from the subject;

means responsive to the echo signals for creating a Doppler image indicating variations in Doppler-shifted frequency spectrum with time;

means for determining a threshold according to the average brightness of a sample region in the Doppler image, the sample region being dominated by noise;

means for tracing the maximum and/or minimum frequency in each Doppler-shifted frequency spectrum in the Doppler image on the basis of the threshold; and means for displaying a trace line together with the Doppler image.

2. The apparatus according to claim 1, wherein the threshold determining means includes means for selecting a region having the lowest average brightness from among a plurality of candidate regions in the Doppler image as the sample region.

3. The apparatus according to claim 2, wherein the candidate regions include a plurality of regions each designed in the form of a rectangle whose long side is parallel to the time axis of the Doppler image and a plurality of regions each designed in the form of a rectangle whose long side is parallel to the frequency axis of the Doppler image.

4. The apparatus according to claim 1, wherein the threshold determining means determines the threshold on the basis of the average brightness and the standard deviation of brightness of the sample region.

5. The apparatus according to claim 4, wherein the threshold is set to the sum of the average brightness and the standard deviation.

6. The apparatus according to claim 1, wherein the trace means searches through each Doppler-shifted frequency spectrum in the Doppler image along its frequency axis from the high-frequency side and identifies a point at which the brightness exceeds the threshold that appears first as a point of the maximum frequency in the Doppler-shifted frequency spectrum.

7. The apparatus according to claim 1, wherein the trace means searches through each Doppler-shifted frequency spectrum in the Doppler image along its frequency axis from the low-frequency side and identifies a point at which the brightness exceeds the threshold that appears first as a point of the minimum frequency in the Doppler-shifted frequency spectrum.

8. The apparatus according to claim 1, further comprising means responsive to the maximum-frequency trace line for determining a contraction phase of the heart.

9. The apparatus according to claim 8, wherein the determining means determines a period of time that the trace line exceeds its maximum value multiplied by a given coefficient as the contraction phase of the heart.

10. The apparatus according to claim 8, further comprising identifying means for identifying at least one of a point of systole maximum bloodstream velocity, a point of end-of-diastole bloodstream velocity, and a point of minimum bloodstream velocity with the contraction phase as a search range.

11. The apparatus according to claim 10, wherein the identifying means identifies a maximum point of the trace line within the search range as the point of systole maximum bloodstream velocity.

12. The apparatus according to claim 10, wherein the identifying means searches through the trace line along the time axis within the search range and identifies a minimum point that appears first as the point of end-of-diastole bloodstream velocity.

13. An ultrasound Doppler diagnostic apparatus comprising:

means for transmitting pulsed beams of ultrasound to a subject under examination and receiving echo signals from the subject;

means responsive to the echo signals for creating a Doppler image indicating variations in Doppler-shifted frequency spectrum with time;

means for extracting a bloodstream range from the Doppler image;

means for tracing the centroid frequency in each Doppler-shifted frequency spectrum within the bloodstream range in the Doppler image; and means for displaying a centroid-frequency trace line together with the Doppler image.

14. The apparatus according to claim 13, wherein the extracting means includes threshold determining means for determining a threshold in accordance with the average brightness of a sample region in the Doppler image, the sample region being dominated by noise, and trace means for tracing the maximum and minimum frequencies in each Doppler-shifted frequency spectrum in the Doppler image on the basis of the threshold, a region between maximum-frequency and minimum-frequency trace lines being the bloodstream range.

15. An ultrasound Doppler diagnostic apparatus comprising:

means for transmitting pulsed beams of ultrasound to a subject under examination and receiving echo signals from the subject;

means responsive to the echo signals for creating a Doppler image indicating variations in Doppler-shifted frequency spectrum with time;

means for tracing the maximum frequency, the minimum frequency or the centroid frequency in each Doppler-shifted frequency spectrum in the Doppler image; and means for identifying specific cardiac events on the basis of a trace line drawn by the trace means.

16. The apparatus according to claim 15, wherein the cardiac events include at least one of a point of systole maximum bloodstream velocity, a point of end-of-diastole bloodstream velocity, and a point of minimum bloodstream velocity.

17. The apparatus according to claim 16, wherein the point of systole maximum bloodstream velocity is identified as a maximum point of the trace line.

18. The apparatus according to claim 16, wherein the point of end-of-diastole bloodstream velocity is identified as a minimum point of the trace line that appears first when it is searched along the time axis.

19. An ultrasound Doppler diagnostic apparatus comprising:

means for transmitting pulsed beams of ultrasound to a subject under examination and receiving echo signals from the subject;

means responsive to the echo signals for creating a Doppler image indicating variations in Doppler-shifted frequency spectrum with time;

means for tracing the maximum frequency, the minimum frequency or the centroid frequency in each Doppler-shifted frequency spectrum in the Doppler image to form a trace line;

means for identifying specific cardiac events on the basis of a trace line formed by the trace means; and means for displaying markers indicating the identified cardiac events in conjunction with the trace line.

20. The apparatus according to claim 19, wherein the cardiac events include at least one of a point of systole maximum bloodstream velocity, a point of end-of-diastole bloodstream velocity, and a point of minimum bloodstream velocity.

* * * * *